United States Patent [19]

McGredy

[11] Patent Number: Plant 5,428

[45] Date of Patent: Apr. 2, 1985

[54] ROSE PLANT 'MACNEWYE'

[76] Inventor: Samuel D. McGredy, 130 B Beach Rd., Castor Bay, Auckland 9, New Zealand

[21] Appl. No.: 518,093

[22] Filed: Jul. 28, 1983

[51] Int. Cl.[3] ..... A01H 5/00

[52] U.S. Cl. ..... Plt./22

[58] Field of Search ..... Plt./22

*Primary Examiner*—James R. Feyrer

*Attorney, Agent, or Firm*—Vincent G. Gioia

[57] ABSTRACT

A new floribunda rose variety of unusual Spanish orange flower coloring blooming primarily in small clusters.

1 Drawing Figure

The present invention relates to a new and distinct variety of rose plant of the floribunda rose class, which was originated by my crossing as seed parent the rose known as "Mary Sumner" and as pollen parent an unnamed and unpatented seedling of my creation. The denomination of this variety is "Macnewye".

Among the novel characteristics possessed by this new variety which distinguish it from its parents and all other varieties of which I am aware are flowers of unusual Spanish orange coloring borne in small sprays. The color is believed to be a first in this range. The brilliant Spanish orange color is set off by deep green foliage. The flower's unique coloring appears more striking because of the plant's prolific blooming habit. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "25A" is plate 25A of The Royal Horticultural Society Colour Chart.

Parentage: Seedling.

*Seed parent.*—"Mary Sumner".

*Pollen parent.*—Unnamed seedling.

Class: Floribunda.

The following observations are made of specimens grown outdoors in Kern County, Califf., during the month of June.

FLOWER

Blooming habit: Continuous.

Bud:

(1) *Size.*—Medium.

(2) *Form.*—High centered, long pointed.

(3) *Color.*—When sepals first divide — near 25A becoming quickly 26B.

(4) *Sepals.*—Longer than bud, fancy.

(5) *Peduncle.*—Length — short. Aspect — upright. Strength — erect (thornless). Color — near 138B (many prickles).

Bloom:

(1) *Size.*—Average size when fully expanded — about 3 inches.

(2) *Borne.*—Singly and in small sprays (clusters).

(3) *Form.*—High centered at first then petals reflex.

(4) *Petalage.*—Number of petals under normal conditions — about 24.

(5) *Color.*—After sepals fall and petals unfurl, predominant flower coloring is Spanish orange 26A to 26B. As flowers open further, petal top surface is primarily 26B; however, some lightening to 26C is seen at outer petals. Also appearing at some petal edges is slight infusion of pink tones. Clusters of petals, as at flower centers, appear deeper orange toned, near 26A, resulting in beautiful orange tones.

Petals:

(1) *Texture.*—Thick.

(2) *Appearance.*—Inside silky and outside satiny.

(3) *Form.*—High centered, exhibition.

(4) *Arrangement.*—Imbricate.

(5) *Petaloids in center.*—Few (2 to 5).

(6) *Persistence.*—Drop off cleanly.

(7) *Fragrance.*—Slight, sweet.

(8) *Lasting quality.*—Excellent on plant and as cut flower.

REPRODUCTIVE ORGANS

Stamens, filaments and anthers:

(1) *Arrangement.*—Stamens regular, arranged around styles, uneven length.

(2) *Color.*—Near 24B.

Pollen:

*Color.*—Near 23A.

Styles: Few, short, even length.

Stigmas:

*Color.*—Near 10B.

Hips:

*Shape.*—Globular.

*Size.*—Small.

*Color.*—Near 28B.

*Do seeds protrude?.*—No.

PLANT

Form: Compact, slightly spreading.

Growth: Vigorous, free branching.

*Height attained.*—About 3 feet.

Foliage: Compound 5 leaflets.

(1) *Size.*—Large (for a floribunda).

(2) *Quantity.*—Abundant with short internodes.

(3) *Color.*—New foliage: Upper side — near 187A. Under side — near 187B. Old foliage: Upper side — near 139B. Under side — near 138B.

(4) *Shape.*—Long, oval, acuminate.

(5) *Texture.*—Upper side is smooth, veins pronounced and under side is glaborous.

(6) *Edge.*—Serrate to doubly serrate.

(7) *Serration.*—Substantial.

(8) *Leaf stem.*—Color — near 144A (midrib prickles). Under side — near 144C.

(9) *Stipules.*—Medium, simple, slightly bearded.

(10) *Resistance to disease.*—Blackspot — excellent. Mildew — excellent. Rust — excellent.

Wood:

(1) *New wood.*—Color — near 145B. Bark — smooth.

(2) *Old wood.*—Color — near 144A. Bark — smooth.

Thorns:

(1) *Thorns.*—Quantity (main stalk) — ordinary. On laterals from stalk — few. Form — long, thin, slight recurve. Length — long. Color — near 144D. Position — irregular.

(2) *Prickles.*—Few on main stem, profuse on laterals.

Winter hardiness: Needs winter protection.

I claim:

1. A new and distinct variety of rose plant of the floribunda class, substantially as shown and described, characterized particularly by unusual Spanish orange flowers borne singly and in small clusters beautifully contrasting with deep green foliage.

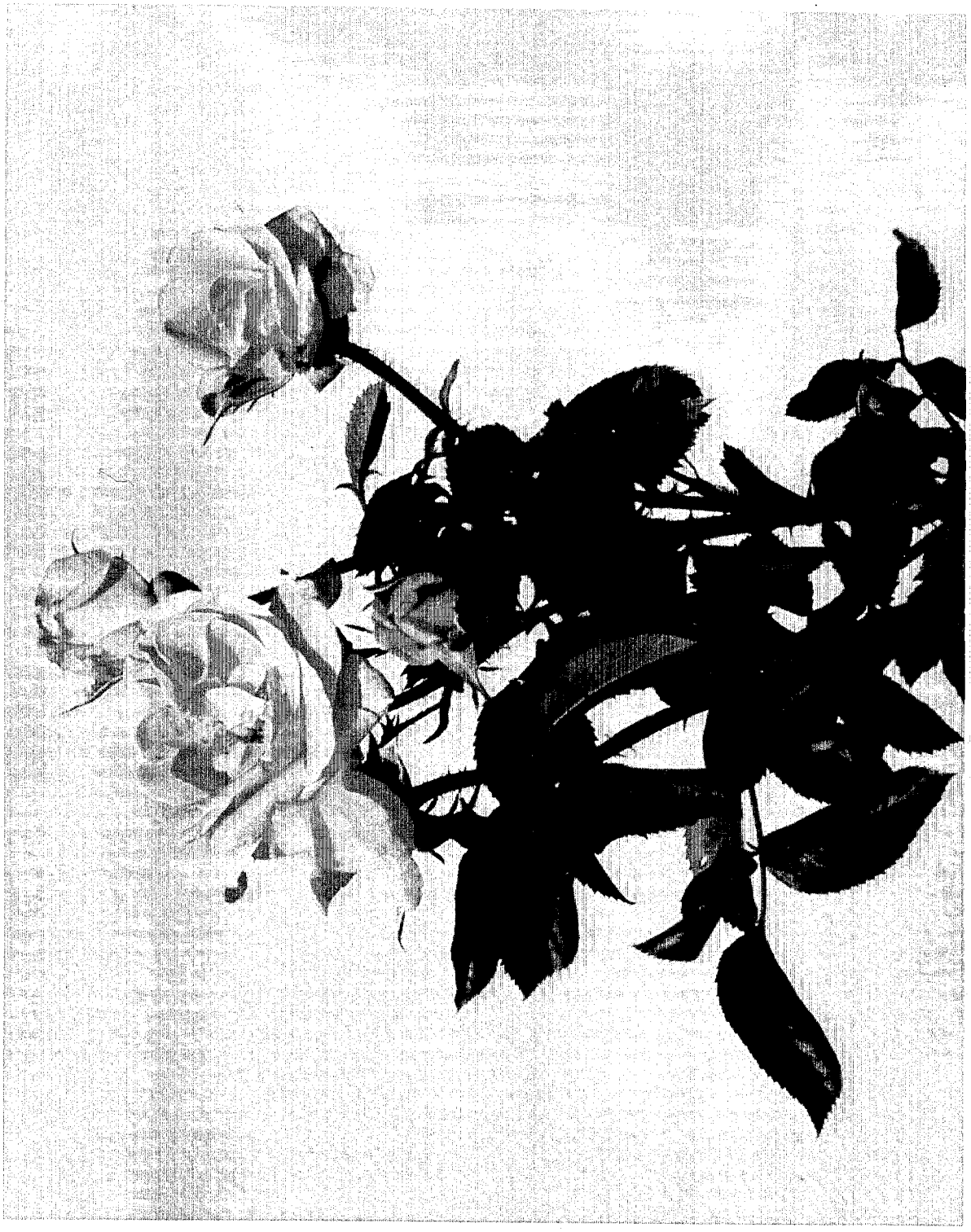

* * * * *